United States Patent
Zhao et al.

(10) Patent No.: US 11,925,474 B2
(45) Date of Patent: Mar. 12, 2024

(54) METHODS AND SYSTEMS FOR PATIENT BASELINE ESTIMATION

(71) Applicant: KONINKLIJKE PHILIPS N.V., Eindhoven (NL)

(72) Inventors: Claire Yunzhu Zhao, Cambridge, MA (US); Bryan Conroy, Cambridge, MA (US); Mohammad Shahed Sorower, Cambridge, MA (US); David Paul Noren, Cambridge, MA (US); Kailash Swaminathan, Bangalore (IN); Chaitanya Kulkarni, Bangalore (IN); Ting Feng, Cambridge, MA (US); Kristen Tgavalekos, Cambridge, MA (US); Emma Holdrich Schwager, Cambridge, MA (US); Erina Ghosh, Cambridge, MA (US); Vinod Kumar, Bangalore (IN); Vikram Shivanna, Bangalore (IN); Srinivas Hariharan, Bangalore (IN); Daniel Craig McFarlane, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 749 days.

(21) Appl. No.: 16/919,154

(22) Filed: Jul. 2, 2020

(65) Prior Publication Data
US 2021/0052217 A1    Feb. 25, 2021

Related U.S. Application Data

(60) Provisional application No. 62/890,386, filed on Aug. 22, 2019.

(51) Int. Cl.
| | | |
|---|---|---|
| *A61B 5/00* | (2006.01) | |
| *G16H 10/60* | (2018.01) | |
| *G16H 50/20* | (2018.01) | |
| *G16H 50/30* | (2018.01) | |
| *G16H 50/50* | (2018.01) | |
| *G16H 50/70* | (2018.01) | |

(52) U.S. Cl.
CPC .......... *A61B 5/4842* (2013.01); *A61B 5/7225* (2013.01); *A61B 5/742* (2013.01); *G16H 10/60* (2018.01); *G16H 50/20* (2018.01); *G16H 50/30* (2018.01); *G16H 50/50* (2018.01); *G16H 50/70* (2018.01)

(58) Field of Classification Search
CPC ........ G16H 50/30; G16H 50/50; G16H 50/20; A61B 5/0205; A61B 5/4842; A61B 5/72–5/7296
See application file for complete search history.

(56) References Cited

U.S. PATENT DOCUMENTS

| | | | | |
|---|---|---|---|---|
| 2008/0162182 A1* | 7/2008 | Cazares | ................. | G16H 50/70 705/2 |
| 2008/0214904 A1* | 9/2008 | Saeed | .................... | G16H 40/63 705/2 |
| 2009/0093686 A1* | 4/2009 | Hu | .......................... | G16Z 99/00 600/300 |
| 2013/0232103 A1* | 9/2013 | Saeed | .................... | G16H 10/20 706/46 |
| 2013/0338543 A1* | 12/2013 | Gegner | .................... | A61B 5/11 600/595 |
| 2019/0209022 A1* | 7/2019 | Sobol | .................... | A61B 5/0022 |
| 2019/0341147 A1* | 11/2019 | Lord | ........................ | A61B 5/01 |

OTHER PUBLICATIONS

Xu, Dongkuan, and Yingjie Tian. "A comprehensive survey of clustering algorithms." Annals of Data Science 2.2 (2015): 165-193. (Year: 2015).*

Simpao, A.F. et al. A Review of Analytics and Clinical Informatics in Health Care. J Med Syst 38, 45 (2014), p. 1-7 (Year: 2014).*

Luo, Jake, et al. "Big data application in biomedical research and health care: a literature review." Biomedical informatics insights 8 (2016): BII-S31559 p. 1-10 (Year: 2016).*

Marcin JP, Pollack MM. "Review of the Acuity Scoring Systems for the Pediatric Intensive Care Unit and Their Use in Quality Improvement". Journal of Intensive Care Medicine. 2007;22(3):131-140 (Year: 2007).*

Kontio, E. et al. "Predicting patient acuity from electronic patient records", Journal of Biomedical Informatics, vol. 51, 2014, pp. 35-40 (Year: 2014).*

Conroy, B. et al., "Patient Similarity Using Population Statistics and Multiple Kernel Learning". Proceedings of Machine Learning for Healthcare, vol. 68, 2017.

* cited by examiner

*Primary Examiner* — G. Steven Vanni (57) ABSTRACT

The present disclosure is directed to systems and methods for developing an individual-specific patient baseline for a target patient. An exemplary method involves: determining one or more acuity scores for the target patient; identifying patient health data corresponding to one or more low acuity time periods; storing retrospective clinical data from a group of patients in a second database; comparing the patient health data corresponding to the one or more low acuity time periods with retrospective clinical data from a group of patients by identifying one or more patient subgroups; determining the individual-specific patient baseline using an adaptive baseline selection algorithm, wherein the adaptive baseline selection algorithm is used to determine whether to determine the individual-specific patient baseline using patient health data or using retrospective clinical data from one or more patient subgroups; and displaying, using a user interface, the individual-specific patient baseline.

15 Claims, 5 Drawing Sheets

METHODS AND SYSTEMS FOR PATIENT BASELINE ESTIMATION

FIELD OF THE INVENTION

The present disclosure is directed to systems and methods for determining individual-specific patient baselines for disease prediction and monitoring, and in particular, using a dynamic model for patient baseline estimation with subgroups of similar patients.

BACKGROUND

Patients exhibit substantial variations in physiology, and accordingly, patients' symptoms and responses to diseases can also vary. Because of these heterogeneous patient characteristics, establishing accurate and individual-specific baselines is important for disease prediction and monitoring algorithms to ensure relevance to the patient and institute correct alert mechanisms appropriate for the patient. It is challenging to determine patient baselines that are useful for clinical practice because physiological conditions differ significantly between patients. Even for the same patient, baselines may vary at different stages of the patient's life (e.g. age), disease conditions, and disease stage, and there is usually not enough data for accurate and personalized determination of baseline, especially at the very beginning of hospital admission. Accordingly, there is a continued need for clinically-meaningful baselines for disease prediction and monitoring of patients.

SUMMARY OF THE INVENTION

The present disclosure is directed to systems and methods for determining individual-specific patient baselines for disease prediction and monitoring, in particular using a dynamic model for patient baseline estimation with subgroups of similar patients. Generally, patient health data regarding one or more health factors for a target patient corresponding to periods of low acuity are collected and compared with clinical data from a group of patients regarding at least the one or more health factors. Subgroups of the group of patients are identified to which the target patient is similar. An adaptive selection algorithm is used to determine whether to calculate the individual-specific patient baseline using the patient health data from the target patient or using retrospective clinical data from one or more patient subgroups, as more patient health data is collected from the target patient and the subgroups to which the patient is similar become more individualized to the target patient.

Generally, in one aspect, a computer implemented method for developing an individual-specific patient baseline for a target patient is provided. The method comprises: determining one or more acuity scores for the target patient, wherein the one or more acuity scores vary based on time; identifying one or more low acuity time periods corresponding to one or more low acuity scores; retrieving patient health data from the target patient regarding one or more health factors; identifying patient health data corresponding to the one or more low acuity time periods; storing patient health data corresponding to the one or more low acuity time periods in a first database; storing retrospective clinical data from a group of patients regarding at least the one or more health factors in a second database; comparing the patient health data corresponding to the one or more low acuity time periods with retrospective clinical data from a group of patients regarding the one or more health factors by identifying one or more patient subgroups, wherein the one or more patient subgroups are subgroups of the group of patients; determining the individual-specific patient baseline using an adaptive baseline selection algorithm, wherein the adaptive baseline selection algorithm is used to determine whether to calculate the individual-specific patient baseline using patient health data or using retrospective clinical data from one or more patient subgroups; and displaying, using a user interface, the individual-specific patient baseline.

In an aspect, the one or more acuity scores are determined using general acuity scoring systems or disease specific scoring systems.

In an aspect, the one or more patient subgroups are identified using patient similarity measures or generic clustering algorithms.

In an aspect, the individual-specific patient baseline is determined using retrospective clinical data from one or more patient subgroups by averaging baselines from the one or more patient subgroups or by computing a weighted average baseline from two or more patient subgroups.

In an aspect, the adaptive baseline selection algorithm utilizes an average length of medical treatment amongst members of the one or more patient subgroups as a factor to determine whether to determine the individual-specific patient baseline using patient health data or using retrospective clinical data from the one or more patient subgroups.

In an aspect, if a length of medical treatment of the target patient is more than 25 percent of the average length of medical treatment amongst members of the one or more patient subgroups, the individual-specific patient baseline is determined using patient health data.

In an aspect, each subgroup of the one or more subgroups comprises one or more sets of retrospective clinical data; wherein variance between the one or more sets of retrospective clinical data can be computed; and wherein the individual-specific patient baseline is determined using the patient health data if the variance in the retrospective clinical data of the one or more subgroups is less than a variance threshold or wherein the individual-specific patient baseline is determined using the patient health data if a population size of the one or more subgroups is less than a size threshold.

In an aspect, the individual-specific patient baseline is determined using the patient health data if a difference between a centroid of a patient subgroup of the one or more patient subgroups and a centroid of a neighboring subgroup is less than a centroid threshold, wherein the neighboring subgroup is a neighboring cluster on a similarity clustering graph.

Generally, in one aspect, a system for developing individual-specific patient baselines for a target patient is provided. The system comprises: a first database in which patient health data corresponding to one or more low acuity time periods corresponding to one or more low acuity scores is stored; a second database in which retrospective clinical data from a group of patients regarding at least one or more health factors is stored; a user interface configured to display the individual-specific patient baseline; and a processor. The processor is configured to: compare the patient health data corresponding to the one or more low acuity time periods with the retrospective clinical data from the group of patients regarding the one or more health factors by identifying one or more patient subgroups, wherein the one or more patient subgroups are subgroups of the group of patients; and determine the individual-specific patient baseline using an adaptive baseline selection algorithm, wherein the adaptive baseline selection algorithm is used to determine whether to calculate the individual-specific patient baseline using patient health data or using retrospective clinical data from one or more patient subgroups.

In an aspect, the one or more acuity scores are determined using general acuity scoring systems or disease specific scoring systems.

In an aspect, the processor is further configured to identify patient subgroups using patient similarity measures or generic clustering algorithms.

In an aspect, the processor is further configured to determine the individual-specific patient baseline using the retrospective clinical data from the one or more patient subgroups by averaging baselines from the one or more patient subgroups or by computing a weighted average baseline from two or more patient subgroups.

In an aspect, the processor is further configured to use an adaptive baseline selection algorithm utilizing an average length of medical treatment amongst members of the one or more patient subgroups as a factor to determine whether to determine the individual-specific patient baseline using patient health data or using the retrospective clinical data from the one or more patient subgroups.

In an aspect, the processor is further configured to determine the individual-specific patient baseline using the patient health data if a variance in the retrospective clinical data of the one or more subgroups is less than a variance threshold or determine the individual-specific patient baseline using the patient health data if a population size of the one or more subgroups is less than a size threshold.

In an aspect, the processor is further configured to determine individual-specific patient baseline using the patient health data if a difference between a centroid of a patient subgroup of the one or more patient subgroups and a centroid of a neighboring subgroup is less than a centroid threshold, wherein the neighboring subgroup is a neighboring cluster on a similarity clustering graph.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

Individuals exhibit substantial variations, such as variations in body core temperature, circadian rhythms, and immune cell phenotype, so that what is considered healthy for one individual may not be necessarily the case for another. Symptoms and responses to disease also vary considerably between individuals. Because of these heterogeneous patient characteristics, establishing accurate and individual-specific baselines is important for disease prediction and monitoring algorithms to ensure relevance to the patient and institute alert mechanisms appropriate for the patient. Determination of patient baselines, however, is challenging because the baselines are to be personalized to a specific individual at the specific time point of their disease trajectory, and this is be done with limited patient data.

The present disclosure is directed to improved systems and methods for determining individual-specific patient baselines for disease prediction and monitoring, and specifically a dynamic model for patient baseline estimation using subgroups of similar patients. The present disclosure also provides an algorithm to adaptively establish personalized baselines as patient information accumulates during the patient's encounter with medical professionals. Generally, patient health data regarding one or more health factors for a target patient corresponding to periods of low acuity are collected and compared with clinical data from a group of patients regarding at least the one or more health factors. Subgroups of the group of patients are identified to which the target patient is similar. An adaptive selection algorithm is used to determine whether to calculate the individual-specific patient baseline using the patient health data from the target patient or using retrospective clinical data from one or more patient subgroups, as more patient health data is collected from the target patient and the subgroups to which the patient is similar become more individualized to the target patient. The estimated baseline can be useful in the diagnosis, risk stratification, patient monitoring, and discharge readiness assessment of the patient.

When a patient is seeking medical treatment, for example during a hospital stay or a stay in an intensive care unit (ICU), one or more acuity scores may be determined throughout the patient's encounter with health care professionals. Acuity scores measure general illness severity and are used, for example, in an intensive care unit or emergency room, to assess resource use, predict outcome, and characterize disease severity. Some acuity scoring systems are specific to one or more diseases or to a system of the body, for example, the Glasgow Coma Scale (GCS), the Mortality Probability Model (MPM), the Multiple Organ Dysfunction Score (MODS), or the Sequential Organ Failure Assessment (SOFA). Other scoring systems are general and measure general disease severity on admission, including the Acute Physiology and Chronic Health Evaluation (APACHE), the Oxford Acute Severity of Illness Score (OASIS), the Acute Physiology Score (APS), the Simplified Acute Physiology Score (SAPS); and scoring systems for assessing medical professionals work load, including Therapeutic Intervention Scoring System (TISS) and Nine Equivalents of Nursing Manpower Use Score (NEMS).

During a patient's stay in an intensive care unit, the patient's condition may vary, and the patient's acuity score may also therefore vary. Higher acuity scores correspond to times when the patient's condition is more severe, and the patient requires more medical resources. Lower acuity scores correspond to times when the patient's condition is less severe and the patient requires less medical care and resources. For example, during a patient's treatment in an intensive care unit, there may be times when the patient undergoes an abrupt adverse change in health, which corresponds to higher acuity scores. As another example, the patient may first enter the ICU in a more severe medical condition, corresponding to a higher acuity score, than later on when the patient's medical situation stabilizes, corresponding to a lower acuity score.

While determining the patient's acuity scores, and during the patient's medical treatment, data may be collected on the patient as part of the patient's medical assessment and treatment. For example, patient health data may be collected regarding various health factors such as the patient's vital statistics, including body temperature, pulse rate, respiration rate, and blood pressure; blood test performed; medical diagnoses; medical imaging; demographic information; etc. This patient health data may be collected over a period of time and may be collected more than once. As an example, patient health data may be obtained for a patient when the patient first enters the ICU regarding the patient's vital statics. A patient's body temperature, pulse rate, respiration rate, and blood pressure may be collected. Over time, the patient's vital statistics may change, for example as the patient's medical condition stabilizes. For example, the vital statistics taken when the patient first entered the intensive care unit, may reflect a worse medical condition than the vital statistics taken of a patient after the patient received some medical treatment and stabilized.

Patient health data corresponding to time periods with the low acuity scores may be identified, collected, and stored in a first database. Patient health data from the time periods when the patient is in a less severe medical state and has lower acuity scores may be more likely to reflect a patient's baseline. A baseline is information or an initial value which is used for comparison with later data. The concept of a baseline is essential to the daily practice of medicine in order to establish a relative rather than absolute meaning to data. A baseline may be used for diagnosis, risk stratification, patient monitoring, and discharge readiness assessment of the patient.

This patient health data can be compared to health data from a group of patient stored in a second database. For example, when other patients are treated for various medical conditions, health data regarding a variety of health factors may be collected. The retrospective clinical data of the group of patients may include values for the one or more health factors which are the subject of the patient health data collected from the target patient. The health data from the group of patients may also include data on clinical measurements taken regarding additional health factors regarding which data from the target patient has not been collected.

Comparison of the patient health data with the retrospective clinical data of the group of patients may involve identifying subgroups of the group of patients with which the patient has similar characteristics. Similar subgroups can be identified using various methods. Patient subgroups can be identified using patient similarity measures such as those described in Bryan Conroy, Minnan Xu-Wilson, Asif Rahman, Patient Similarity Using Population Statistics and Multiple Kernel Learning, *Proceedings of Machine Learning for Healthcare*, Vol. 68, 2017, the entirety of which is incorporated herein by reference, or generic clustering algorithms such as, for example, k-means clustering, mean-shift clustering, density-based spatial clustering, EM clustering, agglomerative hierarchical clustering, and clustering based on t-SNE and PCA. Patient subgroups can be identified using other similarity measures such as cosine or geometric similarity, or dimensionality reduction methods. Patient similarity aims to identify cohorts based on a set of patient characteristics (like demographics, vitals, labs, medical history, and treatments) to enable applications like case-based comparison for clinical decision support. Features characterizing patient state may be relevant or irrelevant to patient similarity depending on the clinical context. Subgroups may be based on combination of vital signs (Heart Rate, systolic blood pressure), laboratory values (Sodium, Lactate, Magnesium), comorbidities and demographics, etc. They may also be features extracted from a latent variable model, for example, features extracted from a hidden layer in a deep neural network.

Identification of patient subgroups may be based on the one or more health factors for which patient data is collected. For example, if data is collected from the patient regarding blood pressure, a subgroup of the similar patients may be identified based on the blood pressure category to which the patient belongs, with a low category having systolic blood pressure less than 90 mm Hg and diastolic blood pressure less than 60 mm Hg, a normal category having systolic blood pressure from 120 to 90 mm Hg and diastolic blood pressure from 80 to 60 mm Hg, an elevated category having systolic blood pressure from 120 to 129 mm Hg and diastolic blood pressure less than 80 mm Hg, a hypertension stage 1 category having systolic blood pressure from 130 to 139 mm Hg and diastolic blood pressure from 80 to 89 mm Hg, a hypertension stage 2 category having systolic blood pressure 140 mm Hg and higher and diastolic blood pressure 90 mm Hg and higher, and a hypertension crisis category having systolic blood pressure higher than 180 mm Hg and/or diastolic blood pressure higher than 120. As another example, if a patient's heart rate is measured as 63 beats per minute, a similar subgroup may comprise people whose heart rate was measured in the range of 58-68 beats per minute. The subgroups to which the patient is similar may vary. It should be appreciated that various other approaches to determining what values are similar can also be used. A subgroup may relate to one or more health variables, or it may not clearly identify any health variable based on which the patients are clustered. A subgroup may also have a small or a large population size. A subgroup may further include a narrow range of member with very specific medical issues, or a subgroup may be broad and include patients with a range of medical issues and a range of values for the health factors regarding which patient health data for the target patient was collected.

During the patient's medical treatment, as more patient health data regarding one or more health factors corresponding to one or more low acuity time periods is identified, the similar patient subgroups can change. As more or different patient health data is gathered, the subgroups may change. The newer subgroups may be subgroups which are more specific to the patient's needs, incorporate data categories or ranges for a greater number and variety of health factors, reflect revised patient data relating to lower acuity time periods, etc.

A baseline for a health factor for a patient may be determined by using the retrospective clinical data from the one or more patient subgroups to which the patient is similar. In that case the centroid for the health factor may be calculated for each subgroup. By identifying subgroups, the group of patients is organized into representative subgroups based upon similar characteristics. Each member of the subgroup has more in common with other members of the same subgroup than with members of the other groups. The most representative point within the subgroup is called the centroid. Often this is the mean of the values of the points of data in the subgroup. The baseline for the target patient may be the averaged centroid for a health factor over the patient subgroups to which the patient is similar. As another example, a weighted average of the centroids for a health factor over the patient subgroups may be calculated to determine the patient baseline for that health factor.

A baseline for a health factor for a patient may be determined using patient data when there is an indication that enough patient data has been collected to obtain an accurate or reliable patient baseline. An adaptive baseline selection algorithm may be used to determine whether to determine the patient baseline using patient health data from the target patient or the using retrospective clinical data from one or more patient subgroups. As an example, a patient baseline may be determined using patient health data after comparing the length of medical stay of the target patient with the average length of medical treatment amongst members of the one or more patient subgroups to which the target patient is similar. For example, if the length of medical treatment of the target patient is above 25 percent of the average length of medical treatment of the patients in the one or more patient subgroups, then the patient baseline can be determined using patient data. A comparison of the length of medical treatment, as an example, the length of hospital stay of a patient, with the average length of medical treatment of the members of the subgroups gives an indication of how much data has been gathered about the target patient compared to other patients who are similar to the target patient. As more data is gathered about the target patient, more information is known about the target patient, and the patient health data may be more robust and reliable.

As another example, the adaptive baseline selection algorithm may determine to calculate the patient baseline using patient health data from the target patient, rather than using retrospective clinical data from one or more patient subgroups, when the population size, for example, the number of clinical patients in a subgroup, of the one or more subgroups to which the target patient is similar is less than a size threshold. If the population size of the one or more patient subgroups is small, this may indicate that the subgroups to which the patient is similar are more specific to the patient's condition.

As another example, the adaptive baseline selection algorithm may determine to calculate the patient baseline using patient health data, rather than using retrospective clinical data from one or more patient subgroups, when the variance in the clinical data of the subgroups to which the patient is similar is less than a variance threshold. The variance in the clinical data of the patients in a subgroup is an indication of the difference in the patients of the subgroup. Less variance in the clinical data of the patients in a subgroup is an indication that the patients in the subgroup are less different from one another. When a subgroup is identified in which the patients are similar to one another, this provides an indication that enough medical data was collected on the patient to identify similar patients with sufficient specificity. For example, when less patient health data from low acuity time periods is available, for example, one set of vital statistics, the patient could be seen as similar to a broad range of other patients. When more data is available about the target patient, for another patient to be similar there may be more criteria to which the similar patients are similar. As a result, the subgroups to which the patient is similar may fit more criteria and be more specific to the patient. A greater degree of similarity may be found because there are more criteria to be similar to, and less variance may be found between the members of the subgroup.

As another example, the patient baseline may be determined using patient health data from the target patient, rather than using retrospective clinical data from one or more patient subgroups, based on a comparison of the patient subgroups to which the patient is similar with neighboring subgroups. Neighboring subgroups are neighboring clusters or groups on a similarity clustering graph, where groups have been identified and groups that are closer to each other are more similar. If the difference or a residual between a centroid of a patient subgroup and a centroid of a neighboring subgroup for one or more health factors is less than a threshold, the centroid threshold, then the patient baseline is determined using the patient health data from the target patient. When the difference between the centroid of a subgroup and the centroid of a neighboring subgroup is small this indicates that the subgroups are very similar, yet also distinct subgroups, which may indicate that the identification of the subgroup involved a high degree of specificity. When there is a high degree of specificity involved in identifying a patient subgroup, this means sufficient low acuity patient data has been identified and collected to have confidence in using the patient health data to determine a patient baseline.

Figure 1:
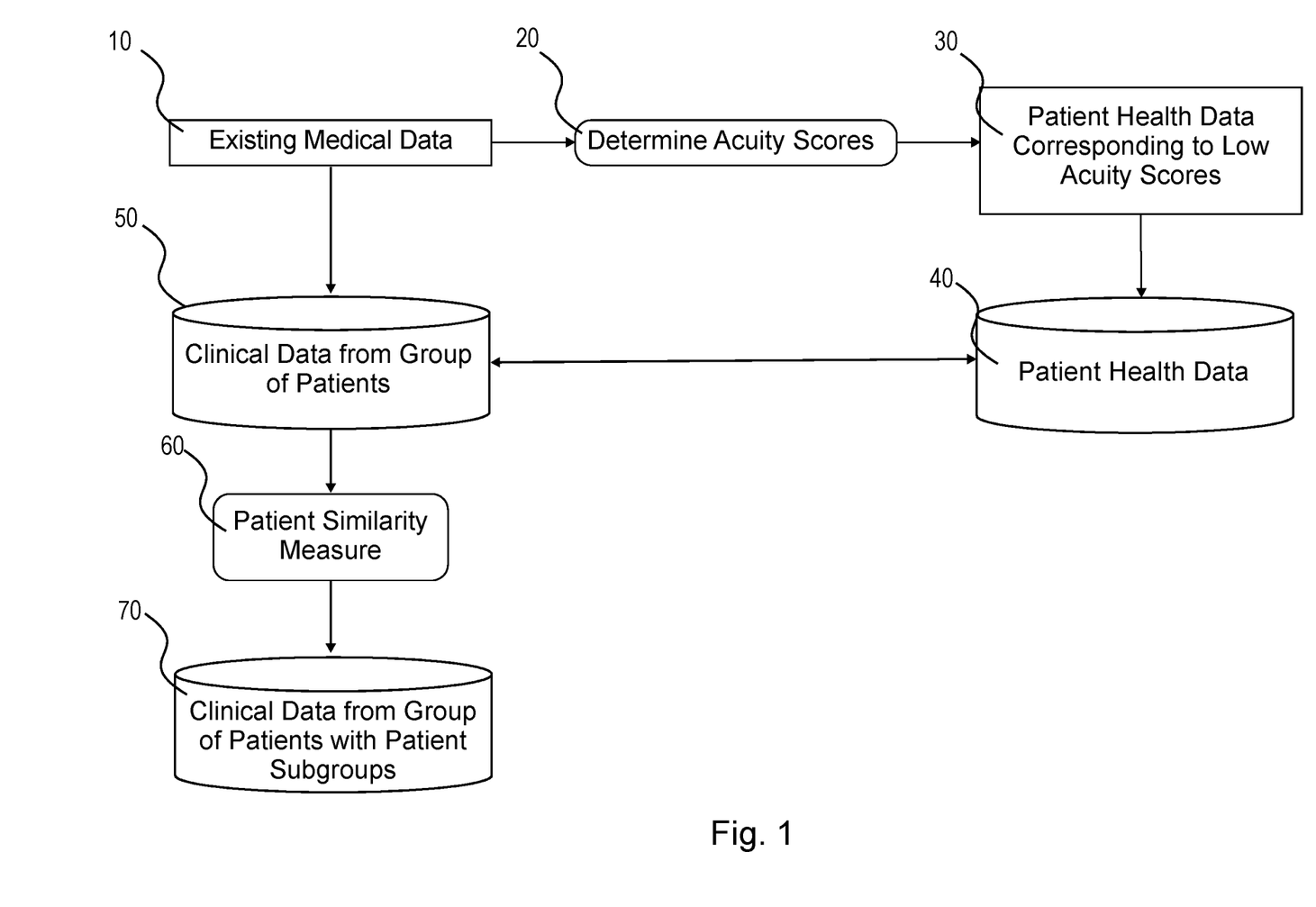
FIG. 1 is a diagram illustrating an exemplary algorithm for developing individual-specific patient baselines according to aspects of the present disclosure.

FIG. 1 is a diagram showing an exemplary algorithm for comparing the patient health data corresponding to the one or more low acuity time periods with retrospective clinical data from a group of patients. Existing medical data 10, for example, patient health data on the target patient, is utilized to determine one or more acuity scores 20 for the target patient. Patient health data 40 corresponding to one or more low acuity time periods 30 is identified and stored in a first database. Retrospective clinical data from a group of patients 50 is gathered from existing medical data and stored in a second database. The retrospective clinical data from a group of patients 50 is compared to the patient health data 40. The comparison is made using patient similarity measures 60. After utilizing the patient similarity measures 60, the clinical data from the group of patients is clustered into subgroups of patients with whom the target patient is similar, shown in box 70.

Figure 2:
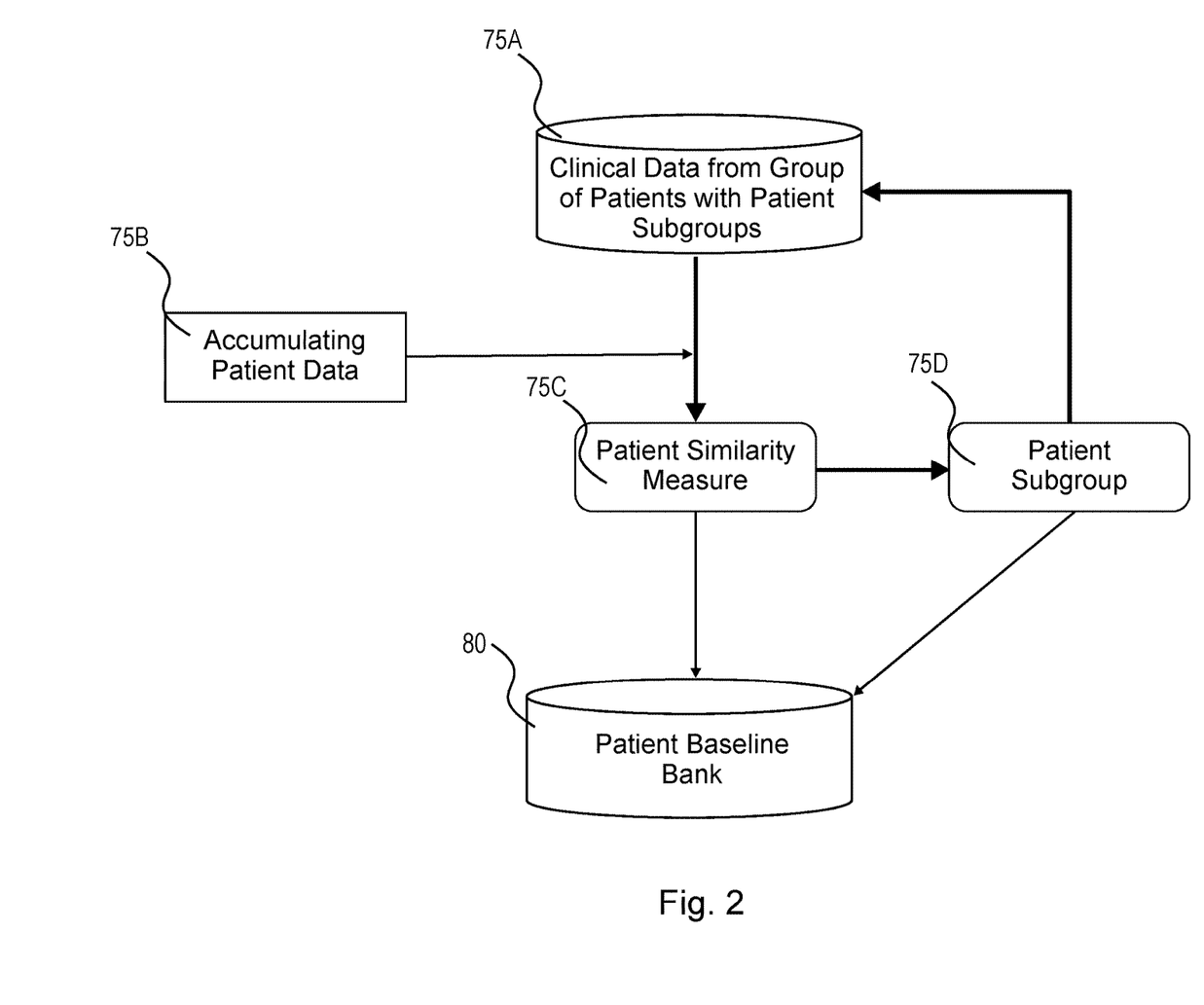
FIG. 2 is a diagram illustrating an exemplary algorithm for developing individual-specific patient baselines according to aspects of the present disclosure.

FIG. 2 is a diagram showing an exemplary algorithm by which individual-specific patient baselines for a target patient are gathered. At step 75, clinical data from a group of patients 75A, which have been clustered into subgroups, and accumulating patient data 75B, which includes additional patient health data 40 on a various health factors, are compared using patient similarity measures 75C. This comparison involves identifying patient subgroups 75D into which the retrospective clinical data from a group of patients 75A is now clustered. As the patient health data on the target patient accumulates, and the accumulating patient data 75B is factored into the identification of similar patient subgroups from retrospective clinical data of a group of patients, more individual-specific patient baselines can be gathered. The individual-specific patient baselines can be gathered and stored in patient baseline bank 80.

Figure 3:
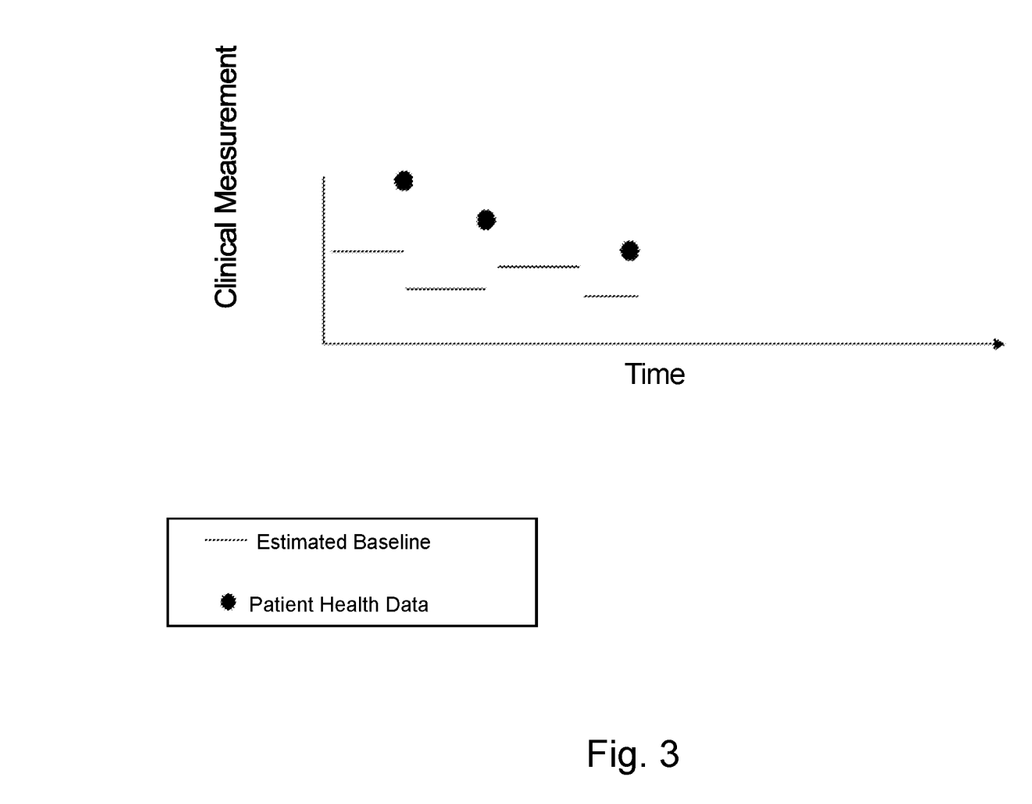
FIG. 3 is a graph illustrating aspects of the method developing individual-specific patient baselines.

FIG. 3 is a graph illustrating the increasing specificity with which patient baselines can be determined as additional data on the target patient is gathered. As additional clinical measurements are taken on the target patient as time progresses, the estimated patient baseline, calculated using retrospective clinical data from one or more patient subgroups to which the target patient is similar, gets closer and closer to patient health data gathered from the target patient.

Figure 4:
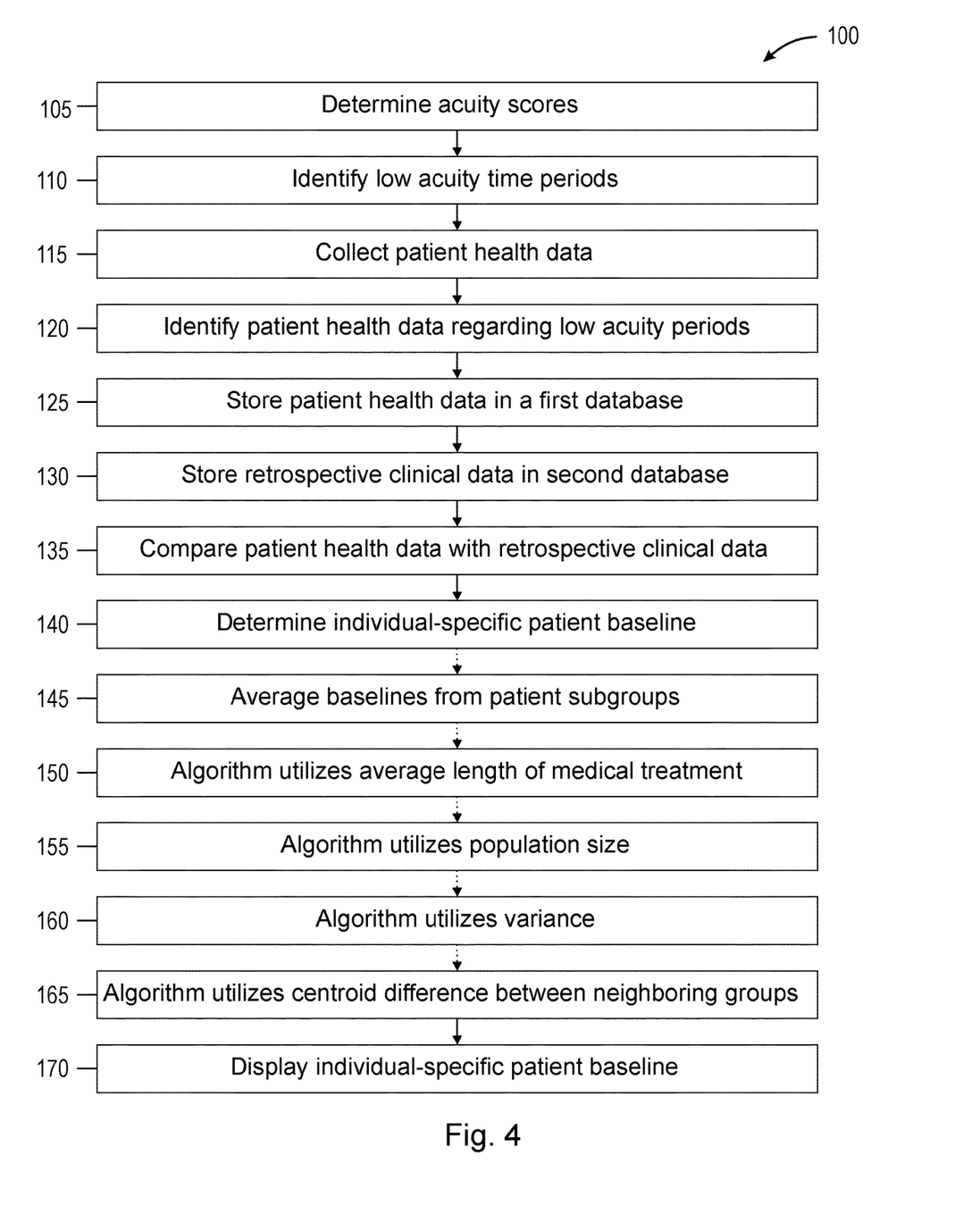
FIG. 4 is a flowchart showing an exemplary method for developing individual-specific patient baselines according to aspects of the present disclosure.

FIG. 4 is a flowchart of an exemplary method 100 for developing an individual-specific patient baseline for a target patient. The system for developing individual-specific patient baselines for a target patient may be any of the systems described or otherwise envisioned herein, and may comprise any of the components described or otherwise envisioned herein. At step 105 of the method, one or more acuity scores for the target patient are determined, wherein the one or more acuity scores vary based on time. At step 110, one or more low acuity time periods corresponding to one or more low acuity scores are identified. Patient health data regarding one or more health factors, where the one or more health factors provide information regarding a patient's health status, are collected at step 115. At step 120, patient health data corresponding to the one or more low acuity time periods is identified. Patient health data corresponding to the one or more low acuity time periods is stored in a first database at step 125. Retrospective clinical data from a group of patients at least regarding the one or more health factors is stored in a second database at step 130. At step 135, the patient health data corresponding to the one or more low acuity time periods is compared with retrospective clinical data from a group of patients regarding the one or more health factors. One or more patient subgroups are identified, where the one or more patient subgroups are subgroups of the group of patients to which the target patient is similar. At step 140, the individual-specific patient baseline is determined using an adaptive baseline selection algorithm. The adaptive baseline selection algorithm is used to determine whether to calculate the individual-specific patient baseline using patient health data or using retrospective clinical data from one or more patient subgroups.

At optional step 145, the individual-specific patient baseline is determined using retrospective clinical data from one or more patient subgroups by averaging baselines from the one or more patient subgroups or by computing a weighted average baseline from two or more patient subgroups. At optional step 150, the adaptive baseline selection algorithm utilizes an average length of medical treatment amongst members of the one or more patient subgroups as a factor to determine whether to determine the individual-specific patient baseline using patient health data or using retrospective clinical data. If a length of medical treatment of the target patient is more than 25 percent of the average length of medical treatment amongst members of the one or more patient subgroups, the individual-specific patient baseline is determined using patient health data. At optional step 155, the individual-specific patient baseline is determined using the patient health data if the variance in the retrospective clinical data of the one or more subgroups is less than a variance threshold. At optional step 160, the individual-specific patient baseline is determined using patient health data if a population size of the one or more subgroups is less than a size threshold. At optional step 165, the individual-specific patient baseline is determined using patient health data if a difference between a centroid of a patient subgroup of the one or more patient subgroups and a centroid of a neighboring subgroup is less than a centroid threshold. The neighboring subgroup is a neighboring cluster on a similarity clustering graph. The individual-specific patient baseline is displayed using a user interface at step 170.

Figure 5:
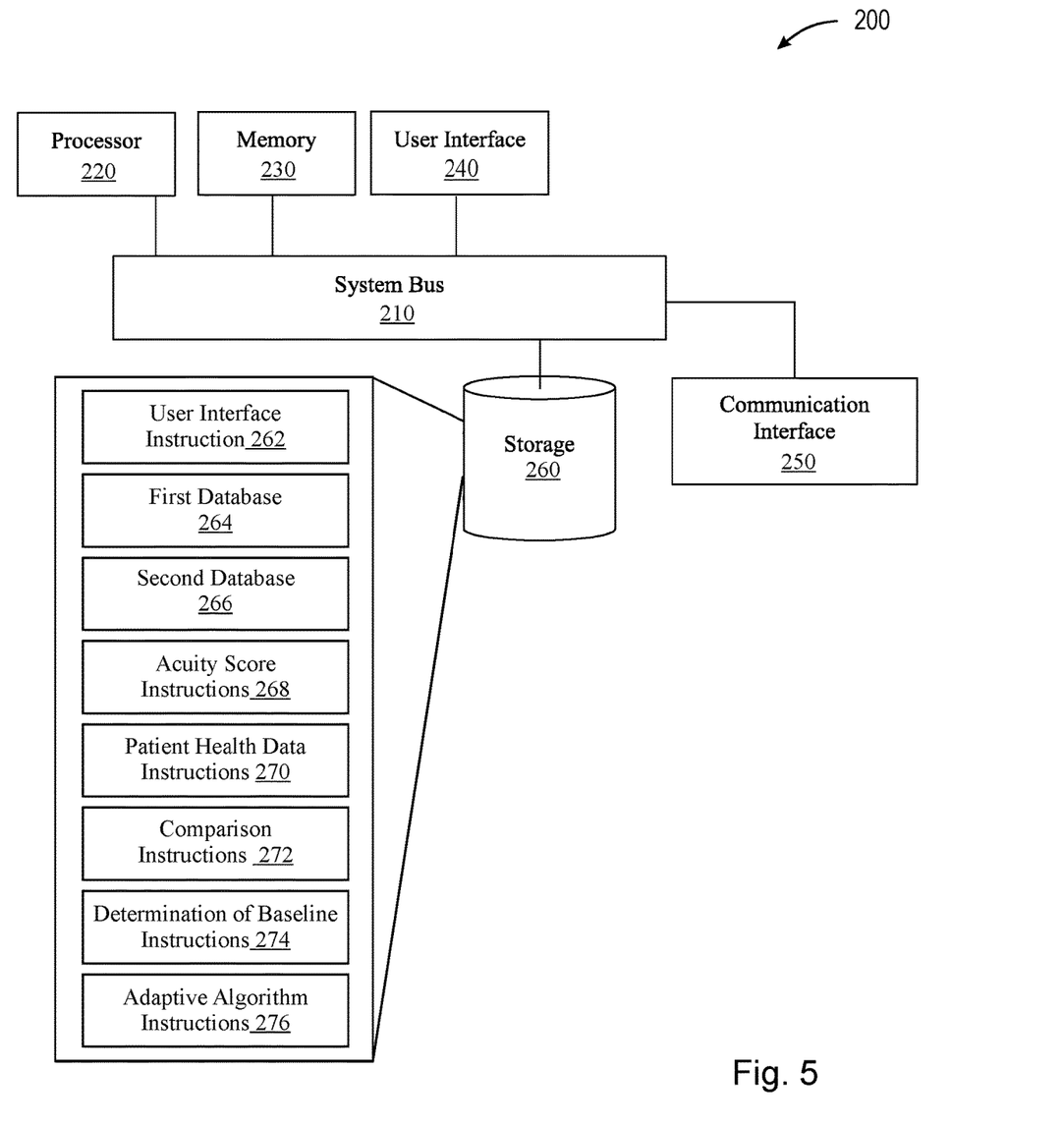
FIG. 5 is schematic representation of system for developing individual-specific patient baselines according to aspects of the present disclosure.

FIG. 5 is an exemplary schematic representation of system 200 for developing individual-specific patient baselines for a target patient. System 200 may be any of the systems described or otherwise envisioned herein, and may comprise any of the components described or otherwise envisioned herein.

According to an embodiment, system 200 comprises one or more of a processor 220, memory 230, user interface 240, communications interface 250, and storage 260, interconnected via one or more system buses 210. It will be understood that the actual organization of the components of the system 200 may be different and more complex than illustrated.

According to an embodiment, system 200 comprises a processor 220 capable of executing instructions stored in memory 230 or storage 260 or otherwise processing data to, for example, perform one or more steps of the method. Processor 220 may be formed of one or multiple modules. Processor 220 may take any suitable form, including but not limited to a microprocessor, microcontroller, multiple microcontrollers, circuitry, field programmable gate array (FPGA), application-specific integrated circuit (ASIC), a single processor, or plural processors.

Memory 230 can take any suitable form, including a non-volatile memory and/or RAM. The memory 230 may include various memories such as, for example L1, L2, or L3 cache or system memory. As such, the memory 230 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of system 200. It will be apparent that, in embodiments where the processor implements one or more of the functions described herein in hardware, the software described as corresponding to such functionality in other embodiments may be omitted.

User interface 240 may include one or more devices for enabling communication with a user. The user interface can be any device or system that allows information to be conveyed and/or received, and may include a display, a mouse, and/or a keyboard for receiving user commands. In some embodiments, user interface 240 may include a command line interface or graphical user interface that may be presented to a remote terminal via communication interface 250. The user interface may be located with one or more other components of the system, or may located remote from the system and in communication via a wired and/or wireless communications network.

Communication interface 250 may include one or more devices for enabling communication with other hardware devices. For example, communication interface 250 may include a network interface card (NIC) configured to communicate according to the Ethernet protocol. Additionally, communication interface 250 may implement a TCP/IP stack for communication according to the TCP/IP protocols. Various alternative or additional hardware or configurations for communication interface 250 will be apparent.

Storage 260 may include one or more machine-readable storage media such as read-only memory (ROM), random-access memory (RAM), magnetic disk storage media, optical storage media, flash-memory devices, or similar storage media. In various embodiments, storage 260 may store instructions for execution by processor 220 or data upon which processor 220 may operate. For example, storage 260 may store an operating system for controlling various operations of system 200.

It will be apparent that various information described as stored in storage 260 may be additionally or alternatively stored in memory 230. In this respect, memory 230 may also be considered to constitute a storage device and storage 260 may be considered a memory. Various other arrangements will be apparent. Further, memory 230 and storage 260 may both be considered to be non-transitory machine-readable media. As used herein, the term non-transitory will be understood to exclude transitory signals but to include all forms of storage, including both volatile and non-volatile memories.

While system 200 for developing individual-specific patient baselines for a target patient is shown as including one of each described component, the various components may be duplicated in various embodiments. For example, processor 220 may include multiple microprocessors that are configured to independently execute the methods described herein or are configured to perform steps or subroutines of the methods described herein such that the multiple processors cooperate to achieve the functionality described herein. Further, where one or more components of system 200 is implemented in a cloud computing system, the various hardware components may belong to separate physical systems. For example, processor 220 may include a first processor in a first server and a second processor in a second server. Many other variations and configurations are possible.

According to an example, storage 260 of multi-locus sequence typing system 200 may store one or more algorithms and/or instructions to carry out one or more functions or steps of the methods described or otherwise envisioned herein. For example, storage 260 may comprise, among other instructions, user interface instructions 262, first database 264, second database 266, acuity score instructions 268, patient health data instructions 270, comparison instructions 272, determination of the individual-specific patient baseline instructions 274, and adaptive baseline selection algorithm instructions 276.

According to an example, user interface instructions 262 direct the system to receive information from and/or provide information to a user via user interface 240. For example, the user interface instructions 262 may be used to receive one or more parameters for generation of acuity scores, identification of low acuity time periods, identification of low acuity scores, collection of patient health data, identification of patient health data corresponding to low acuity time periods, and/or other parameters. The user interface instructions 262 may also direct the system to provide the individual-specific patient baseline to the user.

According to an example, first database 264 is arranged to store patient health data from a target patient corresponding to one or more low acuity time periods, where patient health data relates to one or more health factors and the one or more health factors provide information regarding a patient's health status. According to an example, second database 266 is arranged to store retrospective clinical data from a group of patients at least regarding the one or more health factors.

According to an example, acuity score instructions 268 direct the system to generate one or more acuity scores for the target patient, for example, using general acuity scoring systems or disease specific scoring systems. Acuity score instructions 268 direct the system to identify one or more low acuity time periods corresponding to one or more low acuity scores. Patient health data instructions 270 direct the system to collect patient health data regarding one or more health factors, identify patient health data corresponding to the one or more low acuity time periods, and store patient health data corresponding to the one or more low acuity time periods in the first database. Patient health data instructions 270 also direct the system to store retrospective clinical data from a group of patients at least regarding the one or more health factors in a second database. Comparison instructions 272 direct the system to compare the patient health data corresponding to the one or more low acuity time periods with retrospective clinical data from a group of patients regarding the one or more health factors by identifying one or more patient subgroups to which the target patient is similar. Comparison instructions 272 direct the system to, for example, identify patient subgroups using patient similarity measures or generic clustering algorithms. The determination of the individual-specific patient baseline instructions 274 direct the system regarding how to calculate the individual-specific patient baseline using patient health data or using retrospective clinical data from one or more patient subgroups. The determination of the individual-specific patient baseline instructions 274 direct the system regarding how to calculate the individual-specific patient baseline using retrospective clinical data from one or more patient subgroups by averaging baselines from the one or more patient subgroups or by computing a weighted average baseline from two or more patient subgroups.

As an example, the adaptive baseline selection algorithm instructions 276 direct the system to determine whether to calculate the individual-specific patient baseline using patient health data or using retrospective clinical data from one or more patient subgroups. For example, the adaptive baseline selection algorithm instructions 276 may direct the system to utilize an average length of medical treatment amongst members of the one or more patient subgroups as a factor to determine whether to determine the individual-specific patient baseline using patient health data or using retrospective clinical data from one or more patient subgroups. As another example, the adaptive baseline selection algorithm instructions 276 may direct the system to determine the individual-specific patient baseline using the patient health data if the variance in the retrospective clinical data of the one or more subgroups is less than a variance threshold. As another example, the adaptive baseline selection algorithm instructions 276 may direct the system to determine the individual-specific patient baseline using the patient health data if a population size of the one or more subgroups is less than a size threshold. As another example, the adaptive baseline selection algorithm instructions 276 may direct the system to determine the individual-specific patient baseline using the patient health data if a difference between a centroid of a patient subgroup of the one or more patient subgroups and a centroid of a neighboring subgroup is less than a centroid threshold, where the neighboring subgroup is a neighboring cluster on a similarity clustering graph.

The methods and algorithms disclosed herein may be applied, for example, to infection prediction and/or monitoring of acute episodes in chronic diseases where patients are likely to have repeated visits to Intensive Care Unit (ICU) or General Ward (GW). These baselines will be useful for clinicians in evaluating discharge readiness.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. As used herein in the specification and in the claims, "or" should be understood to have the same meaning as "and/or" as defined above.

It should also be understood that, unless clearly indicated to the contrary, in any methods claimed herein that include more than one step or act, the order of the steps or acts of the method is not necessarily limited to the order in which the steps or acts of the method are recited.

The invention claimed is:

1. A computer implemented method for developing an individual-specific patient baseline for a target patient, comprising:
    determining one or more acuity scores for the target patient, wherein the one or more acuity scores vary based on time;
    identifying one or more low acuity time periods corresponding to one or more low acuity scores;
    retrieving patient health data from the target patient regarding one or more health factors;
    identifying, from the retrieved patient health data, patient health data corresponding to the one or more low acuity time periods;
    storing the patient health data identified as corresponding to the one or more low acuity time periods in a first database;
    storing retrospective clinical data from a group of patients regarding at least the one or more health factors in a second database;
    comparing the patient health data identified as corresponding to the one or more low acuity time periods with retrospective clinical data from a group of patients regarding the one or more health factors by identifying one or more patient subgroups, wherein the one or more patient subgroups are subgroups of the group of patients;
    determining the individual-specific patient baseline using an adaptive baseline selection algorithm based on the patient health data or the retrospective clinical data, wherein the adaptive baseline selection algorithm determines whether to calculate the individual-specific patient baseline using the patient health data or using the retrospective clinical data from one or more patient subgroups; and
    displaying, using a user interface, the individual-specific patient baseline.

2. The method of claim 1, wherein the one or more acuity scores are determined using general acuity scoring systems or disease specific scoring systems.

3. The method of claim 1, wherein one or more patient subgroups are identified using patient similarity measures or generic clustering algorithms.

4. The method of claim 1, wherein the individual-specific patient baseline is determined using retrospective clinical data from one or more patient subgroups by averaging baselines from the one or more patient subgroups or by computing a weighted average baseline from two or more patient subgroups.

5. The method of claim 1, wherein the adaptive baseline selection algorithm utilizes an average length of medical treatment amongst members of the one or more patient subgroups as a factor to determine whether to determine the individual-specific patient baseline using patient health data or using retrospective clinical data from the one or more patient subgroups.

6. The method of claim 5, wherein if a length of medical treatment of the target patient is more than 25 percent of the average length of medical treatment amongst members of the one or more patient subgroups, the individual-specific patient baseline is determined using patient health data.

7. The method of claim 1,
    wherein the individual-specific patient baseline is determined using the patient health data if a variance in the retrospective clinical data of the one or more subgroups is less than a variance threshold or wherein the individual-specific patient baseline is determined using the patient health data if a population size of the one or more subgroups is less than a size threshold.

8. The method of claim 1, wherein the individual-specific patient baseline is determined using the patient health data if a difference between a centroid of a patient subgroup of the one or more patient subgroups and a centroid of a neighboring subgroup is less than a centroid threshold, wherein the neighboring subgroup is a neighboring cluster on a similarity clustering graph.

9. A system for developing individual-specific patient baselines for a target patient, comprising:
    a first database in which patient health data corresponding to one or more low acuity time periods corresponding to one or more low acuity scores is stored;
    a second database in which retrospective clinical data from a group of patients regarding at least one or more health factors is stored;
    a processor configured to:
        compare the patient health data corresponding to the one or more low acuity time periods with the retrospective clinical data from the group of patients regarding the one or more health factors by identifying one or more patient subgroups, wherein the one or more patient subgroups are subgroups of the group of patients; and
        determine the individual-specific patient baseline using an adaptive baseline selection algorithm based on the patient health data or the retrospective clinical data, wherein the adaptive baseline selection algorithm determines whether to calculate the individual-specific patient baseline using the patient health data or using the retrospective clinical data from one or more patient subgroups; and a user interface configured to display the individual-specific patient baseline.

10. The system of claim 9, wherein the one or more acuity scores are determined using general acuity scoring systems or disease specific scoring systems.

11. The system of claim 9, wherein the processor is further configured to identify patient subgroups using patient similarity measures or generic clustering algorithms.

12. The system of claim 9, wherein the processor is further configured to determine the individual-specific patient baseline using the retrospective clinical data from the one or more patient subgroups by averaging baselines from the one or more patient subgroups or by computing a weighted average baseline from two or more patient subgroups.

13. The system of claim 9, wherein the processor is further configured to use an adaptive baseline selection algorithm utilizing an average length of medical treatment amongst members of the one or more patient subgroups as a factor to determine whether to determine the individual-specific patient baseline using patient health data or using the retrospective clinical data from the one or more patient subgroups.

14. The system of claim 9, wherein the processor is further configured to determine the individual-specific patient baseline using the patient health data if a variance in the retrospective clinical data of the one or more subgroups is less than a variance threshold or determine the individual-specific patient baseline using the patient health data if a population size of the one or more subgroups is less than a size threshold.

15. The system of claim 9, wherein the processor is further configured to determine individual-specific patient baseline using the patient health data if a difference between a centroid of a patient subgroup of the one or more patient subgroups and a centroid of a neighboring subgroup is less than a centroid threshold, wherein the neighboring subgroup is a neighboring cluster on a similarity clustering graph.

* * * * *